United States Patent
Walther et al.

(10) Patent No.: US 11,813,425 B2
(45) Date of Patent: Nov. 14, 2023

(54) APPARATUS PERTAINING TO A BASE FOR A VERTICAL SUPPORT POLE

(75) Inventors: Linda M. Walther, Bristol, WI (US); Ishwor P. Adhikari, Mundelein, IL (US); Wthan S. Abernathy, Chicago, IL (US)

(73) Assignee: Medline Industries, LP, Northfield, IL (US)

( * ) Notice: Subject to any disclaimer, the term of this patent is extended or adjusted under 35 U.S.C. 154(b) by 1595 days.

(21) Appl. No.: 13/339,788

(22) Filed: Dec. 29, 2011

(65) Prior Publication Data
US 2013/0168526 A1 Jul. 4, 2013

(51) Int. Cl.
*A61M 5/14* (2006.01)

(52) U.S. Cl.
CPC ....... *A61M 5/1415* (2013.01); *B62B 2207/00* (2013.01); *B62B 2207/02* (2013.01)

(58) Field of Classification Search
CPC .............. A61M 5/1415; A61M 5/1417; A61M 5/1413; A61M 5/1414; A61M 2209/082; A61G 2203/80; A61G 12/008; A61G 7/0503; A61G 12/001; F16M 11/42; F16M 13/022; F16M 2200/08; A47B 87/002; B62B 3/02; B62B 2207/02; B62B 2207/00; B62B 5/0083; F16B 2200/30
USPC .... 248/121, 128, 188.7, 346.01, 519, 125.1, 248/125.8, 129; 446/73, 77, 118; 273/157 R; 211/85.13, 196; D24/128
See application file for complete search history.

(56) References Cited

U.S. PATENT DOCUMENTS

| | | | | |
|---|---|---|---|---|
| 1,893,799 A | * | 1/1933 | Harrincton | B01L 9/00 248/188.7 |
| 2,712,452 A | * | 7/1955 | Bennett | B60D 1/143 280/491.1 |
| 2,823,047 A | * | 2/1958 | Hutchinson | B60D 1/00 280/514 |

(Continued)

FOREIGN PATENT DOCUMENTS

| | | | | |
|---|---|---|---|---|
| CN | 107878520 A | * | 4/2018 | ............ B62B 3/02 |
| DE | 29800696 U1 | * | 3/1998 | ........... B62B 5/0083 |

(Continued)

OTHER PUBLICATIONS

Smartstack Basic I.V. Stand data sheet. Retrieved from Maxtec website, www.maxtecinc.com. We know this information to have been publicly available via the Internet at least as early as Dec. 28, 2010.

*Primary Examiner* — Taylor Morris
(74) *Attorney, Agent, or Firm* — Fitch, Even, Tabin & Flannery LLP (57) ABSTRACT

An IV-pole base has at least one blank and one complimentary tab formed on sides thereof. By one approach, this base comprises, in effect, a jigsaw-puzzle piece that can fully interlock with other such bases in a substantially tessellated manner. So configured, a plurality of IV poles having such a base are easily interlocked with one another to facilitate moving that plurality of IV poles from one place to another. By one approach, the aforementioned blanks and tabs have a substantially circular shape. As one illustrative example, the base comprises a square having two blanks and two tabs, with one such feature formed on each side of the square. By one approach the blanks are formed on sides of the base that are opposite to the tabs.

13 Claims, 4 Drawing Sheets

(56) References Cited

U.S. PATENT DOCUMENTS

| | | | |
|---|---|---|---|
| 3,188,033 A | 6/1965 | Groves | |
| 3,194,426 A * | 7/1965 | Brown, Jr. | B65D 21/0204 |
| | | | 222/143 |
| 3,335,989 A | 8/1967 | Bachmann | |
| 4,008,931 A * | 2/1977 | Kennedy, Jr. | A47B 87/00 |
| | | | 52/592.1 |
| 4,113,222 A * | 9/1978 | Frinzel | F16M 11/28 |
| | | | 248/412 |
| 4,228,897 A * | 10/1980 | Underwood | B65D 67/02 |
| | | | 206/508 |
| 4,253,570 A * | 3/1981 | O'Connor | B65D 85/04 |
| | | | 206/391 |
| 4,266,765 A * | 5/1981 | Sandoval | A61G 12/00 |
| | | | 280/47.371 |
| 4,511,157 A * | 4/1985 | Wilt, Jr. | A61G 5/10 |
| | | | 280/304.1 |
| 4,511,158 A * | 4/1985 | Varga | A61G 7/05 |
| | | | 248/229.11 |
| 4,564,732 A * | 1/1986 | Lancaster | B41J 5/105 |
| | | | 200/293 |
| 4,770,297 A * | 9/1988 | Chang | B65D 85/28 |
| | | | 206/379 |
| 4,807,412 A | 2/1989 | Frederiksen | |
| 4,889,254 A * | 12/1989 | Vola | A45C 7/0045 |
| | | | 132/294 |
| 4,993,330 A * | 2/1991 | Yen | B65D 19/0095 |
| | | | 108/56.1 |
| 5,050,755 A * | 9/1991 | Strawder | B65D 21/0202 |
| | | | 220/909 |
| 5,110,147 A * | 5/1992 | Gershman | B65F 1/1468 |
| | | | 280/79.5 |
| 5,125,607 A | 6/1992 | Pryor | |
| 5,137,237 A | 8/1992 | Haskins | |
| D332,311 S * | 1/1993 | Redding | D24/128 |
| 5,344,169 A | 9/1994 | Pryor | |
| 5,413,236 A * | 5/1995 | Kenevan | B65D 21/083 |
| | | | 220/4.27 |
| 5,421,548 A * | 6/1995 | Bennett | A61G 5/10 |
| | | | 248/129 |
| 5,431,509 A * | 7/1995 | Anderson | A61M 5/1413 |
| | | | 248/225.11 |
| 5,533,697 A * | 7/1996 | Fletcher et al. | 248/146 |
| 5,556,065 A * | 9/1996 | Wadley | A61G 12/008 |
| | | | 248/129 |
| 5,704,625 A * | 1/1998 | Presnell | B60D 1/00 |
| | | | 280/79.5 |
| 5,765,707 A * | 6/1998 | Kenevan | B65D 11/1873 |
| | | | 220/4.31 |
| 5,820,086 A * | 10/1998 | Hoftman | A61M 5/1415 |
| | | | 248/295.11 |
| 5,855,285 A * | 1/1999 | Laird | B25H 3/003 |
| | | | 206/378 |
| 5,857,685 A | 1/1999 | Phillips | |
| D407,929 S * | 4/1999 | Woodring | D3/313 |
| 5,979,844 A | 11/1999 | Hopkins | |
| 6,006,935 A * | 12/1999 | Driver | B65D 21/0204 |
| | | | 220/564 |
| 6,022,088 A | 2/2000 | Metzler | |
| 6,032,590 A | 3/2000 | Chen | |
| 6,042,080 A | 3/2000 | Shepherd | |
| 6,095,348 A * | 8/2000 | Karashima | A47F 5/103 |
| | | | 211/175 |
| 6,179,260 B1 | 1/2001 | Ohanian | |
| 6,182,580 B1 | 2/2001 | Barrett | |
| 6,481,679 B1 * | 11/2002 | Bennett | A61G 13/101 |
| | | | 248/223.41 |
| 6,550,794 B1 * | 4/2003 | Spindel | B60D 1/00 |
| | | | 280/33.993 |
| 6,561,530 B2 * | 5/2003 | Carbonero | A63C 17/26 |
| | | | 403/364 |
| 6,601,860 B2 | 8/2003 | Potter | |
| D479,818 S * | 9/2003 | Gladden, III | B62H 3/08 |
| | | | D12/115 |
| 6,619,599 B2 | 9/2003 | Elliott | |
| 6,666,427 B2 * | 12/2003 | Hennessey | F16M 11/16 |
| | | | 248/125.8 |
| 6,669,224 B2 * | 12/2003 | Newkirk | A61G 12/008 |
| | | | 280/504 |
| 6,682,055 B1 * | 1/2004 | Tomlinson | E01F 13/022 |
| | | | 248/129 |
| 6,719,161 B1 * | 4/2004 | Craig | B65D 25/56 |
| | | | 222/143 |
| 6,722,673 B1 * | 4/2004 | Hamlin | A47B 21/06 |
| | | | 108/50.01 |
| 6,726,033 B2 * | 4/2004 | Sparkowski | A47F 13/085 |
| | | | 211/205 |
| 6,929,588 B2 * | 8/2005 | Hobson | A63B 1/00 |
| | | | 273/458 |
| 6,974,140 B2 * | 12/2005 | Neuman | B62B 3/108 |
| | | | 403/322.2 |
| 6,981,680 B1 | 1/2006 | Gordon | |
| 7,014,384 B2 | 3/2006 | Nicoletti | |
| 7,207,532 B1 * | 4/2007 | Roberts | F16C 11/10 |
| | | | 248/125.1 |
| 7,416,363 B2 * | 8/2008 | Kozhuev | F16B 5/008 |
| | | | 52/592.1 |
| 7,641,158 B2 | 1/2010 | Ferguson | |
| 7,648,147 B2 * | 1/2010 | Lauer | B62B 3/02 |
| | | | 280/47.35 |
| 7,798,501 B1 | 9/2010 | Hopkins | |
| 7,833,077 B1 * | 11/2010 | Simmons, Jr. | 446/85 |
| 8,261,925 B2 * | 9/2012 | Murphy | B65D 21/0204 |
| | | | 220/23.4 |
| 8,317,204 B2 * | 11/2012 | Meers | B62B 3/02 |
| | | | 280/79.11 |
| 8,523,204 B2 * | 9/2013 | Chen | B62B 5/0093 |
| | | | 280/87.021 |
| 8,573,428 B2 * | 11/2013 | Furuta | B65D 21/0212 |
| | | | 220/23.8 |
| 8,899,604 B2 * | 12/2014 | Orenstein | A63C 17/0033 |
| | | | 280/200 |
| 9,290,300 B2 * | 3/2016 | Hendrickson | E04H 7/22 |
| 9,421,835 B2 * | 8/2016 | Kao | A63C 17/265 |
| 9,737,654 B2 | 8/2017 | Walther | |
| 10,369,273 B2 * | 8/2019 | Koehler | A61M 5/1415 |
| 10,577,150 B2 * | 3/2020 | Millhouse | B62B 5/0404 |
| 2003/0106969 A1 | 6/2003 | Dillon | A61M 5/1415 |
| | | | 248/157 |
| 2004/0011941 A1 * | 1/2004 | Roepke et al. | 248/519 |
| 2005/0016044 A1 * | 1/2005 | Kubicek | A47G 1/142 |
| | | | 40/745 |
| 2005/0159784 A1 * | 7/2005 | Arceta | A61G 12/001 |
| | | | 607/20 |
| 2006/0053725 A1 | 3/2006 | Su | |
| 2006/0163829 A1 * | 7/2006 | Livengood | A61B 50/13 |
| | | | 280/87.021 |
| 2006/0278770 A1 * | 12/2006 | MacLeod | A47B 21/00 |
| | | | 248/122.1 |
| 2007/0267551 A1 * | 11/2007 | Townsend | A61M 5/1415 |
| | | | 248/311.2 |
| 2008/0084041 A1 * | 4/2008 | Dukes | B62B 3/04 |
| | | | 280/79.5 |
| 2008/0234116 A1 * | 9/2008 | Elzerman | A63B 21/015 |
| | | | 482/123 |
| 2008/0296443 A1 * | 12/2008 | Lunitz et al. | 248/65 |
| 2008/0302585 A1 * | 12/2008 | Perelli | B62B 5/0076 |
| | | | 180/14.1 |
| 2009/0085317 A1 * | 4/2009 | Livengood | A61H 3/04 |
| | | | 280/79.3 |
| 2009/0146027 A1 * | 6/2009 | Zitting et al. | 248/176.1 |
| 2009/0314906 A1 | 12/2009 | Cote | |
| 2010/0006718 A1 * | 1/2010 | Meyers | A61M 5/1415 |
| | | | 248/125.8 |
| 2010/0007250 A1 * | 1/2010 | Sharpe | A61G 12/001 |
| | | | 312/209 |
| 2010/0043334 A1 | 2/2010 | Rodriguez Alcaine | |
| 2010/0052274 A1 | 3/2010 | West | |

(56) References Cited

U.S. PATENT DOCUMENTS

| | | | | |
|---|---|---|---|---|
| 2010/0109268 A1* | 5/2010 | Koehler | .................. | B62B 3/008 |
| | | | | 280/33.991 |
| 2010/0121170 A1* | 5/2010 | Rule | .................... | A61B 5/1427 |
| | | | | 600/365 |
| 2010/0187785 A1* | 7/2010 | Knappe | ................ | A61G 12/001 |
| | | | | 280/47.34 |
| 2010/0207442 A1* | 8/2010 | Hrib | ..................... | A47C 13/005 |
| | | | | 297/440.14 |
| 2010/0219615 A1* | 9/2010 | Forrest | ..................... | B62B 3/02 |
| | | | | 280/638 |
| 2011/0133417 A1 | 6/2011 | Rouillard | | |
| 2011/0240806 A1* | 10/2011 | Crager et al. | ................. | 248/146 |
| 2012/0119045 A1* | 5/2012 | Gaal | ................... | A61M 5/1415 |
| | | | | 248/219.4 |
| 2012/0223479 A1 | 9/2012 | Pabon | | |
| 2012/0267869 A1* | 10/2012 | Hassell | ..................... | B62B 3/02 |
| | | | | 29/428 |
| 2013/0221630 A1* | 8/2013 | Tavolino | .................. | B62B 3/10 |
| | | | | 280/79.2 |
| 2013/0330164 A1* | 12/2013 | Bushey | ............... | A61M 5/1413 |
| | | | | 280/411.1 |
| 2014/0076910 A1* | 3/2014 | McConnell | ............ | B65D 85/84 |
| | | | | 220/737 |
| 2014/0361129 A1 | 12/2014 | Gomez | | |
| 2016/0270530 A1 | 9/2016 | Heyring | | |
| 2017/0361013 A1* | 12/2017 | Koehler | ............... | F16M 11/043 |
| 2022/0097747 A1* | 3/2022 | Beckwith | .................. | B62B 3/02 |

FOREIGN PATENT DOCUMENTS

| | | | | |
|---|---|---|---|---|
| DE | 29903247 U1 * | 7/1999 | ........... | B62B 5/0083 |
| DE | 29816515 U1 * | 1/2000 | ............... | B60D 1/00 |
| DK | 168857 B1 * | 6/1994 | | |
| EP | 0807541 A1 * | 11/1997 | ............. | B60D 99/00 |
| EP | 2366927 A1 * | 9/2011 | ........... | A61M 5/1415 |
| GB | 2458115 A * | 9/2009 | ............... | B62B 3/02 |
| GB | 2458115 A | 9/2009 | | |
| GB | 2481649 A * | 1/2012 | ................ | A61M 5/14 |
| KR | 200481495 Y1 * | 10/2016 | ........... | A61M 5/1414 |

* cited by examiner

APPARATUS PERTAINING TO A BASE FOR A VERTICAL SUPPORT POLE

TECHNICAL FIELD

This invention relates generally to vertical support poles and more particularly to intravenous poles.

BACKGROUND

Intravenous (IV) poles are known in the art. IV poles typically comprise a base that supports a vertically-disposed pole. The pole, in turn, typically has arms, hooks, or other features upon which medical-services providers can hang, for example, bags of intravenous fluids, medications, and various electro-mechanical apparatuses. IV poles are typically provided in considerable numbers at medical-services facilities such as hospitals, urgent care centers, nursing homes, rehabilitation centers, and so forth.

IV poles are typically, by design, portable. Many IV poles are mounted on casters or other rollers to facilitate moving the pole from place to place. This portability well suits the ordinary use of such an apparatus in a service-care environment. For any number of reasons it may be convenient or even essential that a given IV pole be moved from one place to another. As one simple example in these regards, a single IV pole may move as a corresponding patient moves from a pre-operation staging area to the operating room and then to a recovery area.

Unfortunately, this same portability also gives rise to inconvenience and problems. IV poles tend to move, for example, from initial patient service areas to other floors or areas where the patient continues to receive services for follow-on hours or days. When the patient eventually leaves, however, the IV pole may simply remain in its last location of use. In the absence of attention to relocating such IV poles, local shortages of IV poles can occur in a facility that, in fact, has plenty of IV poles. Accordingly, maintenance personnel are often charged with gathering up currently unused IV poles and returning those poles to places of need or likely need.

Unfortunately, while many IV poles are designed to be easily moved, most are only designed to be moved in isolation. This can make it difficult for a maintenance person to simultaneously move a relatively large number of IV poles (such as, for example, four, six, or a dozen) from one place to another. In some cases the IV poles have vertical legs and maintenance personnel stack or otherwise intertwine those legs to attempt make it easier to move a plurality of such poles at the same time. That said, this intertwining of vertical elements can yield uncertain connections, can be challenging to untwine, and can even raise the center of gravity for the intertwined poles and thereby make it easier for the poles to topple during movement.

BRIEF DESCRIPTION OF THE DRAWINGS

The above needs are at least partially met through provision of the apparatus pertaining to a base for a vertical support pole described in the following detailed description, particularly when studied in conjunction with the drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, an IV pole base can be configured to receive a bottom portion of a vertical support pole and can further have at least one blank and one complimentary tab formed on sides thereof. By one approach, this base comprises, in effect, a jigsaw-puzzle piece that can fully interlock with other such bases in a substantially tessellated manner. So configured, a plurality of IV poles having such a base are easily horizontally interlocked with one another to facilitate moving that plurality of IV poles from one place to another.

By one approach, the aforementioned blanks and tabs have a substantially circular shape. As one illustrative example, the base comprises a square having two blanks and two tabs, with one such feature formed on each side of the square. By one approach the blanks are formed on sides of the base that are opposite to the tabs.

To facilitate ease of movement, by one approach the base can have a plurality of casters coupled to an underside thereof.

By one approach, these bases can be provided in a plurality of colors. This color coding can facilitate easily returning the IV poles to their primary initial-use stations. For example, green bases can correlate to an emergency-services area while blue bases can belong to a maternity wing.

So configured, a large number of IV poles can be easily, quickly, and securely attached to one another to facilitate moving those poles, as a group, from place to place. These IV poles can just as easily be disconnected from one another. By interlocking at a same vertical level from one base to the next, the center of gravity remains constant and helps to avoid toppling the IV poles during movement. These teachings are readily and economically applied with respect to a variety of existing IV pole designs and hence can serve to leverage the continued viability of those existing designs. These teachings are also highly scalable and will work with a wide variety of vertical support poles.

Figure 1:
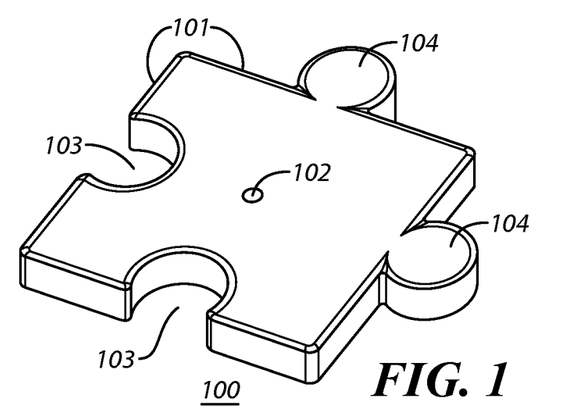
FIG. 1 comprises a perspective view as configured in accordance with various embodiments of the invention.

These and other benefits may become clearer upon making a thorough review and study of the following detailed description. Referring now to the drawings, and in particular to FIG. 1, an illustrative apparatus that is compatible with many of these teachings will be presented.

The illustrated apparatus comprises a base 100 configured to receive a bottom portion of a vertical support pole. This can comprise, for example, a hole 102 disposed through the base 100 to receive such a bottom portion. By one approach, this hole 102 can have internal threads to permit the pole to be threadably engaged with the base 100 to thereby secure the former to the latter. There are other ways to couple a vertical support pole to such a base 100, however. As the present teachings are not particularly sensitive in these regards, further discussion on this point will not be presented here for the sake of brevity.

Figure 2:
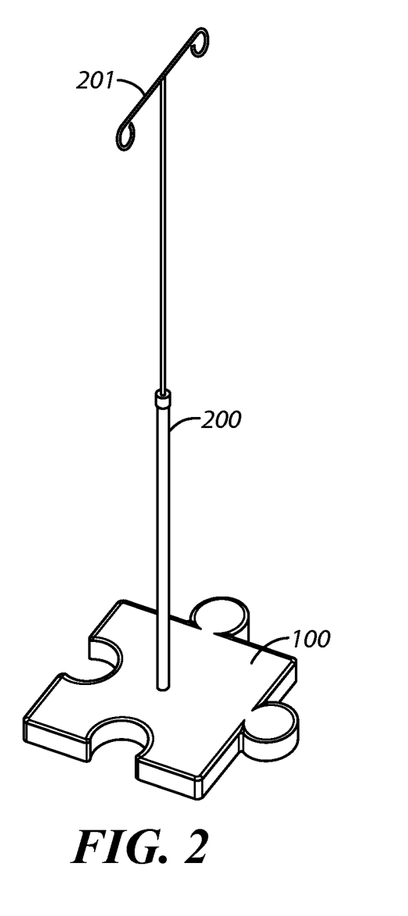
FIG. 2 comprises a perspective view as configured in accordance with various embodiments of the invention.

FIG. 2 presents an illustrative example in these regards. In this example a vertical support pole 200 that comprises an IV pole having support arms 201 connects to the base 100 by so engaging the aforementioned hole 102 in the base 100. So configured, the base 100 and pole 200 are physically connected to one another and hence can be moved as a unit by moving either one or the other as desired.

Figure 3:
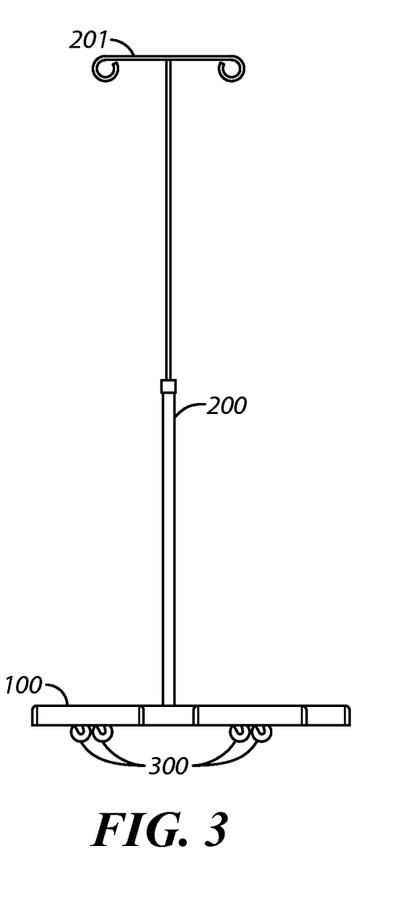
FIG. 3 comprises a side-elevational view as configured in accordance with various embodiments of the invention.
Figure 4:
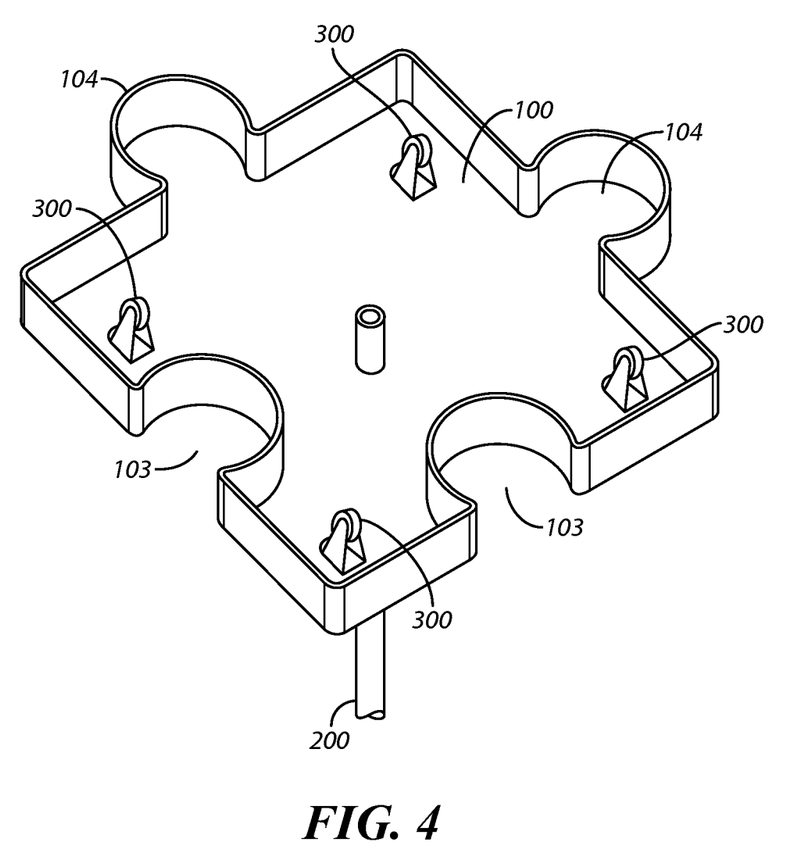
FIG. 4 comprises a bottom perspective view as configured in accordance with various embodiments of the invention.

To facilitate such movement, the base 100 can include one or more rolling elements. By way of illustration and without intending any limitations in these regards, this qcan comprise attaching a plurality of casters 300 to the underside of the base 100 as shown in FIGS. 3 and 4. Though other wheeled components can serve in these regards, casters can be particularly useful as casters can rotate about a support shaft. This, in turn, permits casters to facilitate ease of movement in essentially any direction. In this illustrative example, the base 100 has one such caster 300 disposed in each corner of the square that comprises the base 100.

Referring again to FIG. 1, in this illustrative example the base 100 comprises a square having four sides 101. Other shapes are possible, of course, including a variety of rectangles as well as other regular and irregular shapes. The relative dimensions of the base 100 can vary with the needs of a given application setting. By one approach, these sides 101 can be from around eight inches in length to about eighteen inches in length. The height of the base 100 can vary as well from about half an inch to three inches or so.

This base 100 can be comprised of any of a variety of materials. Examples include, but are not limited to, any of a variety of plastics or metals to natural materials such as wood. By one approach the base 100 comprises a molded plastic component.

This base 100 has at least one blank 103 formed on a side 101 thereof as well as at least one tab 104 formed on another side 101 thereof. A "blank" comprises an opening into the base 100 whereas a "tab" comprises an extension away from the base 100. In this illustrative example the blank 103 and tab 104 are complimentary to one another. This means that the tab 104 has a shape and size that is essentially the same as the shape and size of the blank 103.

By one approach the base 100 has at least two such blanks 103 and two such tabs 104. As illustrated, these tabs 104 can be formed on sides 101 of the base 100 that are opposite to the blanks 103. The present teachings will accommodate other practices in these regards, however. It would be possible, for example, to have a base 100 with two or three blanks 103 and only a single tab 104. As another illustrative example, it would be possible for the base 100 to have two tabs 104 and only a single blank 103.

The blanks/tabs can have whatever shape may be desired. As pictured, and as one illustrative example in these regards, these elements can have a substantially circular shape. That said, and again, other shapes can be readily accommodated. Generally speaking, the shape should be such that two such bases 100 are physically interlocked with one another when the tab 104 of one such base 100 is interlocked with a corresponding and complimentary blank 103 of another such base 100.

Figure 5:
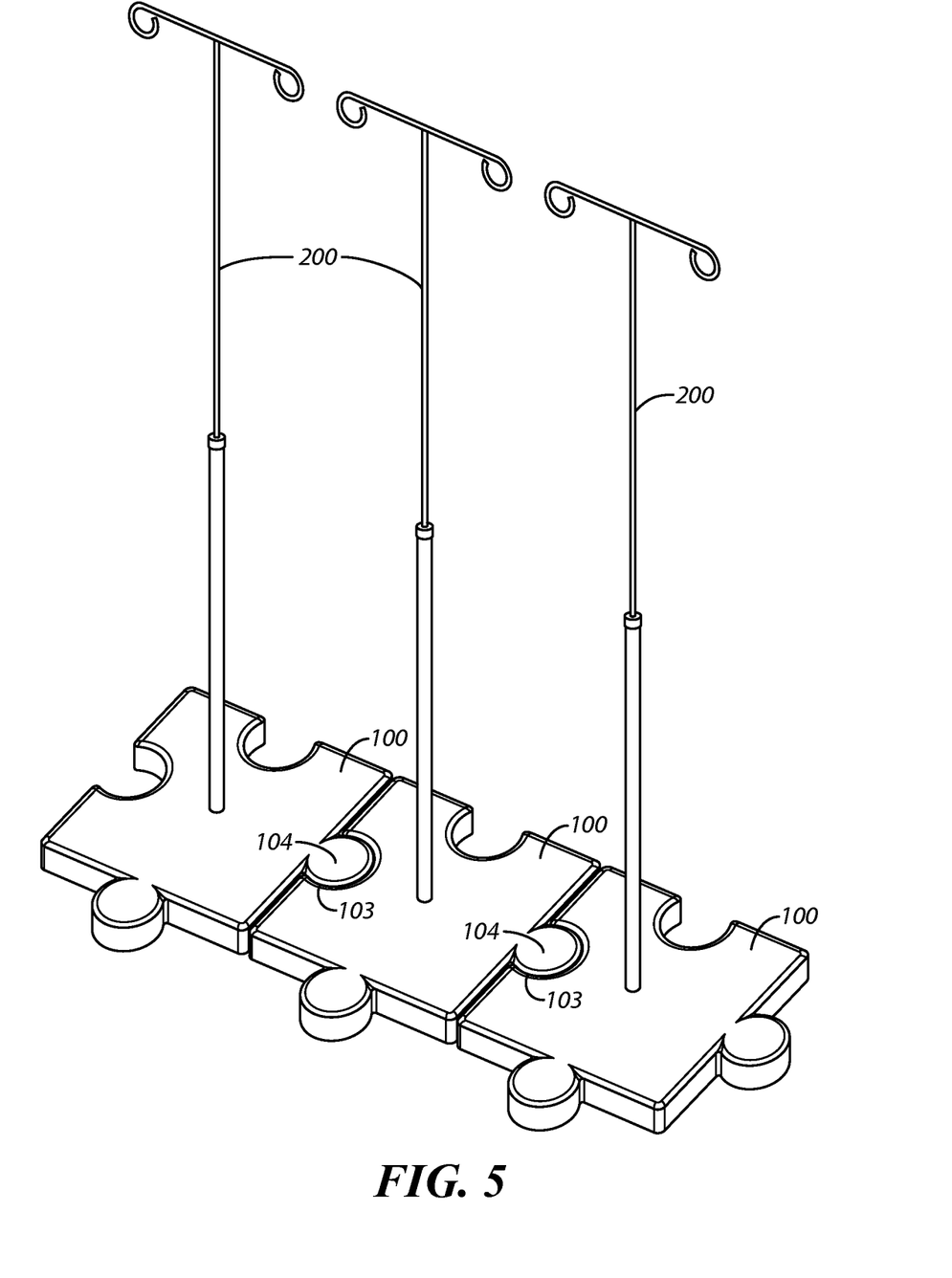
FIG. 5 comprises a perspective view as configured in accordance with various embodiments of the invention.

FIG. 5 provides an illustrative example in these regards. In this example three such bases 100 are interlocked one to the other by interlocking a tab 104 of one base 100 to a blank 103 of an adjacent base 100. In this particular example these bases 100 interlock with one another like jigsaw-puzzle pieces in a substantially tessellated manner such that adjacent bases 100 are juxtaposed one to the other without substantial overlap or gaps.

Being interlocked in this manner, horizontally moving one of the bases 100 will cause the remaining bases 100 to move horizontally as well; as one base 100 moves so move the remaining bases 100. So configured, for example, a maintenance person can easily attach additional bases 100 by simply interlocking tabs 104 and blanks 103 and move the attached bases 100 from place to place to thereby return the IV poles 200 to their respective appropriate locations. Bases 100 can be easily disconnected from such an assembly as desired to thereby singulate the base 100 and leave the corresponding IV pole 200 at a particular location.

There are no strict limits as to how many bases 100 can be joined in this manner into a single assembly. It will also be noted that the bases 100 can all be joined in a single line (as shown) or with at least some bases 100 interconnected to the sides of such a collection.

By one approach at least some of these bases 100 can be color coded. Yellow bases 100, for example, can correspond to a first area of a given facility while red bases 100 can correspond to a second, different area of that facility. The use of such color coding can facilitate identifying IV poles that should be moved to a different location as well as the particular destination to which the IV pole should be moved. These teachings will accommodate using other identifiers as well if desired, such as text or graphic elements such as representative icons or the like.

So configured, a plurality of vertical support poles, such as IV poles, can be easily connected and disconnected from one another to permit and facilitate moving a plurality of such poles from one location to another. The secure interlock can ensure that the bases 100 remain connected to one another while moving an aggregation of such poles, even when moving over small perturbations and gaps in the floor.

Figure 6:
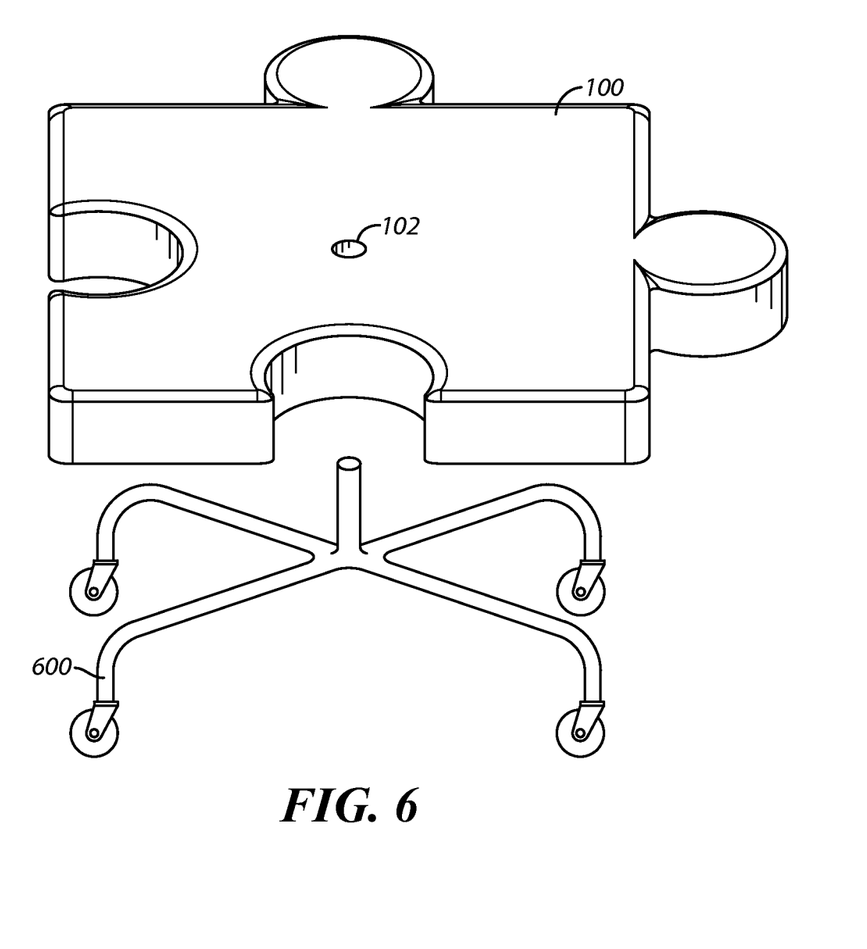
FIG. 6 comprises a perspective view as configured in accordance with various embodiments of the invention.

The described approaches can be economically realized and can also be used with existing IV poles to improve the continued use and viability of those poles. As one illustrative example in these regards, and referring to FIG. 6, the base 100 can be configured to fit over and attach to a primary base 600 for a vertical support pole. This might comprise using snaps or other attachment mechanisms on the underside of the base 100 that can securely interconnect with the elements of such a primary base 600.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:
1. A portable intravenous (IV) pole apparatus comprising:
 a solitary vertically-disposed IV pole having at least two intravenous fluid bag support arms outwardly disposed therefrom;
 an IV pole base configured to support only a single vertically-disposed IV pole and having:
 a centrally-located IV pole interface comprising an internally-threaded hole formed in the IV pole base and configured to receive and secure one end of the solitary vertically-disposed IV pole to the IV pole base;

a plurality of sides, wherein at least one of the sides has a solitary curved-edge blank formed thereon and at least another of the sides has a solitary curved-edge tab formed thereon, wherein the blank and the tab are complimentary to one another; and a plurality of floor-contacting rollers disposed on an underside of the IV pole base apart from the solitary curved-edge tab.

2. The IV pole apparatus of claim 1 wherein the IV pole base is comprised of plastic.

3. The IV pole apparatus of claim 2 wherein the IV pole base comprises a molded plastic component.

4. The IV pole apparatus of claim 1 wherein each of the sides of the plurality of sides has either the solitary curved-edge blank formed thereon or the solitary curved-edge tab formed thereon.

5. The IV pole apparatus of claim 1 wherein the IV pole base comprises a square-shaped base.

6. The IV pole apparatus of claim 1 wherein the IV pole base has a height of between 0.5 inches to three inches.

7. The IV pole apparatus of claim 1 wherein the IV pole base has a number of the solitary curved-edge blanks that is equal to the number of the solitary curved-edge tabs.

8. The IV pole apparatus of claim 1 wherein the IV pole base has a number of the solitary curved-edge blanks that is different than the number of the solitary curved-edge tabs.

9. The IV pole apparatus of claim 1 wherein the IV pole base has an even number of the solitary curved-edge blanks.

10. The IV pole apparatus of claim 1 wherein the IV pole base has an odd number of the solitary curved-edge blanks.

11. The IV pole apparatus of claim 1 wherein the IV pole base has a total number of the solitary curved-edge blanks and the solitary curved-edge tabs that does not exceed four.

12. The IV pole apparatus of claim 1 wherein the IV pole base has a total number of the solitary curved-edge blanks and the solitary curved-edge tabs that does not exceed three.

13. The IV pole apparatus of claim 1 wherein the IV pole base has its complete upper surface even and free from upwardly-extending features aside from the solitary vertically-disposed IV pole.

* * * * *

UNITED STATES PATENT AND TRADEMARK OFFICE
CERTIFICATE OF CORRECTION

| | | |
|---|---|---|
| PATENT NO. | : 11,813,425 B2 | |
| APPLICATION NO. | : 13/339788 | |
| DATED | : November 14, 2023 | |
| INVENTOR(S) | : Linda M. Walther, Ishwor P. Adhikari and Ethan S. Abernathey | |

It is certified that error appears in the above-identified patent and that said Letters Patent is hereby corrected as shown below:

On the Title Page (75) Inventors: delete "Wthan S. Abernathy" and insert --Ethan S. Abernathey--.

Signed and Sealed this
Ninth Day of January, 2024

Katherine Kelly Vidal
*Director of the United States Patent and Trademark Office*